(12) United States Patent
Gopal et al.

(10) Patent No.: US 10,143,693 B2
(45) Date of Patent: Dec. 4, 2018

(54) DOSING REGIMEN FOR MISSED DOSES FOR LONG-ACTING INJECTABLE PALIPERIDONE ESTERS

(71) Applicant: JANSSEN PHARMACEUTICALS, INC., Titusville, NJ (US)

(72) Inventors: Srihari Gopal, Belle Mead, NJ (US); Paulien Gerarda Maria Ravenstijn, Waalre (NL); Alberto Russu, Lange Nieuwstraat (BE); Mahesh Narain Samtani, Flemington, NJ (US)

(73) Assignee: Janssen Pharmaceuticals, Inc., Beerse (BE)

( * ) Notice: Subject to any disclaimer, the term of this patent is extended or adjusted under 35 U.S.C. 154(b) by 0 days.

(21) Appl. No.: 15/090,889

(22) Filed: Apr. 5, 2016

(65) Prior Publication Data

US 2017/0281629 A1    Oct. 5, 2017

Related U.S. Application Data

(60) Provisional application No. 62/162,596, filed on May 15, 2015, provisional application No. 62/144,054, filed on Apr. 7, 2015.

(51) Int. Cl.
*A61K 31/519* (2006.01)
*A61K 9/00* (2006.01)
*A61K 9/14* (2006.01)

(52) U.S. Cl.
CPC .......... *A61K 31/519* (2013.01); *A61K 9/0019* (2013.01)

(58) Field of Classification Search
None
See application file for complete search history.

(56) References Cited

U.S. PATENT DOCUMENTS

| | | |
|---|---|---|
| 5,158,952 A | 10/1992 | Janssen et al. |
| 5,254,556 A | 10/1993 | Janssen et al. |
| 6,077,843 A | 6/2000 | Francois et al. |
| 6,555,544 B2 | 4/2003 | Francois et al. |
| 2009/0163519 A1 | 6/2009 | Vermeulen et al. |
| 2011/0105536 A1 | 5/2011 | Lewyn-Briscoe et al. |
| 2012/0277253 A1 | 11/2012 | Sprogoe et al. |

FOREIGN PATENT DOCUMENTS

| | | |
|---|---|---|
| EP | 2529757 B1 | 8/2014 |
| WO | WO 2006/114384 A1 | 2/2006 |

OTHER PUBLICATIONS

International Search Report re: PCT/US16/24841 dated Mar. 30, 2016.
Osborne et al. "Health-related quality of life advantage of long-acting injectable and antipsychotic treatment for schizophrenia: a time trade-off study". *Health and Quality of Life Outcome*, pp. 1-9, 2012, 10:35.

*Primary Examiner* — Bong-Sook Baek (57) ABSTRACT

The present application provides a method for treating patients in need of psychiatric treatment, wherein said patient is being treated with the 3-month formulation of paliperidone palmitate and fails to take the next scheduled dose of the 3-month formulation of paliperidone palmitate.

29 Claims, 7 Drawing Sheets

DOSING REGIMEN FOR MISSED DOSES FOR LONG-ACTING INJECTABLE PALIPERIDONE ESTERS

CROSS-REFERENCE TO RELATED APPLICATIONS

This application claims priority from U.S. Application No. 62/144,054, filed on Apr. 7, 2015 and Application No. 62/162,596, filed on May 15, 2015, each of which is incorporated herein by reference

FIELD OF THE INVENTION

This invention relates to a method for treating patients who have missed a treatment of 3-month paliperidone palmitate extended-release injectable suspension formulation.

BACKGROUND OF THE INVENTION

Antipsychotic medications are the mainstay in the treatment of schizophrenia, schizoaffective disorder, and schizophreniform disorders. Antipsychotics were first introduced in the mid-1950s. These typical or first generation drugs are usually effective in controlling the positive symptoms of schizophrenia, but are less effective in moderating the negative symptoms or the cognitive impairment associated with the disease. Atypical antipsychotics or second generation drugs, typified by risperidone and olanzapine, were developed in the 1990s, and are generally characterized by effectiveness against both the positive and negative symptoms associated with schizophrenia.

Paliperidone palmitate is the palmitate ester of paliperidone (9-hydroxy-risperidone), a monoaminergic antagonist that exhibits the characteristic dopamine $D_2$ and serotonin (5-hydroxytryptamine type 2A) antagonism of the second generation, atypical antipsychotic drugs. Paliperidone (9-OH risperidone) is the major active metabolite of risperidone. Extended release (ER) osmotic controlled release oral delivery (OROS) paliperidone, as a tablet formulation, is marketed in the United States (U.S.) for the treatment of schizophrenia and maintenance of effect.

3-monthly Paliperidone palmitate is being developed as a long-acting, intramuscular (i.m.), injectable aqueous nanosuspension for the treatment of schizophrenia and other related diseases that are normally treated with antipsychotic medications. Because of extreme low water solubility, paliperidone esters such as paliperidone palmitate dissolve slowly after an i.m. injection before being hydrolyzed to paliperidone and made available in the systemic circulation.

Many patients with the mental illnesses achieve symptom stability with available oral antipsychotic medications; however, it is estimated that up to 75% have difficulty adhering to a daily oral treatment regimen, i.e. adherence problems. Problems with adherence often result in worsening of symptoms, suboptimal treatment response, frequent relapses and re-hospitalizations, and an inability to benefit from rehabilitative and psychosocial therapies. Once monthly Paliperidone palmitate injection has been developed to provide sustained plasma concentrations of paliperidone, which may greatly enhance compliance with dosing. Paliperidone palmitate formulated as an aqueous nanosuspension is described in U.S. Pat. Nos. 6,077,843 and 6,555,544. In addition, a dosing regimen of paliperidone palmitate for treating patients is disclosed in US Patent Application Publication No. 20090163519.

Paliperidone palmitate is an atypical antipsychotic drug administered by injection. The original formulation of paliperidone palmitate was a once-monthly antipsychotic and was approved for the treatment of schizophrenia in adults in numerous countries. The acute and sustained efficacy and tolerability profile of once-monthly paliperidone palmitate has been demonstrated in clinical studies totalling more than 3800 patients. Continued treatment with once-monthly paliperidone palmitate in patients who initially responded to it for acute worsening of symptoms resulted in a nearly 4-fold reduction in relapse risk compared with patients randomized to placebo. A recently developed 3-month formulation offers a substantially longer dosing interval: injections are administered once every 3 months. This extended dosing interval offers the prospect of fewer opportunities for nonadherence than currently available long acting injectable formulations, thus reducing relapse risk as a result of subtherapeutic plasma concentration and its associated negative consequences in patients with schizophrenia.

Even with a drug administered once every 3 months or every 12 weeks (±3 weeks) or 13 weeks±2, patients at time miss their doses of medication. Consequently, there is a need to reinitiate a dosing regimen for patients who miss their regularly scheduled dose of medication. Thus, the objective of the present application is to provide a dosing regimen of paliperidone palmitate for patients in need of a treatment who have missed their 3 month (±2 weeks) dose of paliperidone palmitate 3-month extended-release injectable suspension.

SUMMARY OF THE INVENTION

In one embodiment of the present invention there is provided a dosing regimen for administering an injectable paliperidone palmitate depot to a patient in need of psychiatric treatment that has been treated with a 3-month injectable paliperidone palmitate depot, wherein said patient misses for a period of between about four months and about nine months (inclusive e.g. four months or more but nine months or less) the next scheduled maintenance dose of the 3-month injectable paliperidone palmitate depot, comprising:

(1) administering intramuscularly in the deltoid muscle of said patient a first reinitiation loading dose of the monthly injectable paliperidone palmitate depot on day one;

(2) administering intramuscularly in the deltoid or gluteal muscle of said patient a second reinitiation dose of the monthly injectable paliperidone palmitate depot on about the $8^{th}$ day±4 (e.g. 4th day to about the 12th day) after administering of said first reinitiation loading dose; and

| Missed PP3M dose | Administer PP1M, two doses (into deltoid muscle) | | Then administer PP3M (into deltoid$^a$ or gluteal muscle) Maintenance Dose |
|---|---|---|---|
| | First Reinitiation Dose | Second Reinitiation Dose | |
| 175 mg eq. | 50 mg eq. | 50 mg eq. | 175 mg eq. |
| 263 mg eq. | 75 mg eq. | 75 mg eq. | 263 mg eq. |
| 350 mg eq. | 100 mg eq. | 100 mg eq. | 350 mg eq. |
| 525 mg eq. | 100 mg eq. | 100 mg eq. | 525 mg eq. |

(3) administer intramuscularly in the deltoid or gluteal muscle of said patient the 3-month formulation of paliperidone palmitate in the range of about 175 mg eq. to about 525 mg eq. on about the 30th day±7 (e.g. 23rd day to about the 37th day) after administering of the second reinitiation dose of monthly injectable paliperidone palmitate.

In another embodiment of the present invention there is provided a dosing regimen for administering an injectable paliperidone palmitate depot to a patient in need of psychiatric treatment that has been treated with a 3-month injectable paliperidone palmitate depot, wherein said patient misses for a period of more than nine months the next scheduled maintenance dose of the 3-month injectable paliperidone palmitate depot, comprising:

(1) administering intramuscularly in the deltoid muscle of said patient a first reinitiation loading dose of 150 mg eq. of the monthly injectable paliperidone palmitate depot;

(2) administering intramuscularly in the deltoid muscle of said patient a second reinitiation loading dose of 100 mg eq. the monthly injectable paliperidone palmitate depot on about the 4th day to about the 12th day after administering of said first reinitiation loading dose;

(3) administering intramuscularly in the deltoid or gluteal muscle of said patient a first reinitiation maintenance dose of 50 mg eq. to about 150 mg eq. of the monthly injectable paliperidone palmitate depot on about the 23th day to about the 37rd day after administering of said second reinitiation loading dose;

(4) administering intramuscularly in the deltoid or gluteal muscle of said patient a second reinitiation maintenance dose of from about 50 mg eq. to about 150 mg eq. of monthly injectable paliperidone palmitate depot on about the 23rd day to about the 37th day after administering of the first maintenance additional dose;

(5) administering intramuscularly in the deltoid or gluteal muscle of said patient a third reinitiation maintenance dose of from about 50 mg eq. to about 150 mg eq. of monthly injectable paliperidone palmitate depot on about the 23rd day to about the 37th day after administering of the second maintenance dose; and (6) administering intramuscularly in the deltoid or gluteal muscle of said patient from about 175 mg eq. to about 525 mg eq. of the 3-month formulation of paliperidone palmitate on about the 23rd day to about the 37th day after administering of the third maintenance dose of monthly injectable paliperidone palmitate.

Additional maintenance doses may be administered before the readministration of the 3-month formulation of paliperidone palmitate (e.g. a fourth maintenance dose, fifth maintenance dose).

This and other objects and advantages of the present invention may be appreciated from a review of the present application.

DETAILED DESCRIPTION OF FIGURES

DETAILED DESCRIPTION 3-month paliperidone palmitate extended-release injectable suspension is an antipsychotic medication which is the ester of the active ingredient paliperidone. Paliperidone is effective for the treatment of psychosis and has been used to treat schizophrenia and schizoaffective disorders. The 3-month paliperidone palmitate extended-release injectable suspension suitable for the treatment of psychotic disorders including but not limited to schizophrenia and/or schizoaffective disorders. It is recommended that the 3-month paliperidone palmitate extended-release injectable suspension be administrated to patients who have been adequately treated with the 1-month paliperidone palmitate extended-release injectable suspension (e.g. INVEGA SUSTENNA®) for a several months and it is recommended for at least four months.

3-month paliperidone palmitate extended-release injectable suspension preferably will be provided with an adequate dose of paliperidone palmitate generally in the range of about 250 mg to about 900 mg of paliperidone palmitate to provide a sustained therapeutic concentration of paliperidone over the three month dosing interval to the patient. Preferably the aqueous extended-release suspension for intramuscular injection will be provided in dose strengths of about 273 mg, 410 mg, 546 mg, and 819 mg paliperidone palmitate. The drug product hydrolyzes to the active moiety, paliperidone, resulting in dose strengths of 175 mg eq., 263 mg eq., 350 mg eq., and 525 mg eq. of paliperidone, respectively. 3-month paliperidone palmitate extended-release injectable suspension is preferably provided in a prefilled syringe (cyclic-olefin-copolymer) prefilled with either 175 mg eq. (0.875 mL), 263 mg eq. (1.315 mL), 350 mg eq. (1.75 mL), or 525 mg eq. (2.625 mL) paliperidone (as 273 mg, 410 mg, 546 mg, or 819 mg paliperidone palmitate) suspension with a plunger stopper and tip cap (bromobutyl rubber), a backstop, and 2 types of commercially available needles: a thin walled 22G, 1½-inch safety needle and a thin walled 22G, 1-inch safety needle.

3-month paliperidone palmitate extended-release injectable suspension is intended for intramuscular use only. It is not recommended not to administer by any other route. Care should be taken to avoid inadvertent injection into a blood vessel. Dose should be administered in a single injection; it should not be administered in divided injections as this would change the release profile and has not been studied in clinical trials. It is preferred that injections be administered slowly, deep into the deltoid or gluteal muscle. 3-month paliperidone palmitate extended-release injectable suspension is preferred to be administered using only the thin wall needles to reduce the risk of blockage.

Deltoid Injection

Currently the recommended needle size for administration of 3-month paliperidone palmitate extended-release injectable suspension into the deltoid muscle is determined by the patient's weight:

For patients weighing less than 90 kg, the 1-inch, 22 gauge thin wall needle is recommended.

For patients weighing 90 kg or more, the 1½-inch, 22 gauge thin wall needle is recommended.

It is currently preferred that 3-month paliperidone palmitate extended-release injectable suspension be administer into the center of the deltoid muscle. It is also preferred that deltoid injections should be alternated between the two deltoid muscles.

Gluteal Injection

Currently, the preferred needle size for administration of 3-month paliperidone palmitate extended-release injectable suspension into the gluteal muscle is the 1½-inch, 22 gauge thin wall needle regardless of patient weight. It is preferred that 3-month paliperidone palmitate extended-release injectable suspension be administered into the upper-outer quadrant of the gluteal muscle. It is also preferred that gluteal injections should be alternated between the two gluteal muscles.

Incomplete Administration

To avoid an incomplete administration of 3-month paliperidone palmitate extended-release injectable suspension, it is recommended that to ensure that doses are completely administered that the syringes be vigorously shaken and/or mechanical agitated to obtain a uniform dispersion of the suspension, preferably the suspension will be shaken vigorously for at least 15 seconds within 5 minutes prior to administration to ensure a homogeneous suspension and ensure the needle does not get clogged during injection.

It is preferred that 3-month paliperidone palmitate extended-release injectable suspension is to be used only after the 1-month paliperidone palmitate extended-release injectable suspension (e.g. INVEGA SUSTENNA®) has been established as adequate treatment for at least four months. In order to establish a consistent maintenance dose, it is preferred that at least the last two doses of 1-month paliperidone palmitate extended-release injectable suspension be the same dosage strength before starting 3-month paliperidone palmitate extended-release injectable suspension.

The preferred time to initiate dosing a patient with 3-month paliperidone palmitate extended-release injectable suspension is when the next 1-month paliperidone palmitate dose was to be scheduled with a 3-month paliperidone palmitate extended-release injectable suspension dose based on the previous 1-month injection dose as shown in Table 1. 3-month paliperidone palmitate extended-release injectable suspension may be administered up to about 7 days before or after the monthly time point of the next scheduled paliperidone palmitate 1-month dose.

TABLE 1

Conversion From the Last 1-Month Paliperidone Palmitate Extended-Release Injectable Suspension (INVEGA SUSTENA ®) Dose To the 3-Month Paliperidone Palmitate Extended-Release Injectable Suspension (INVEGA TRINZA ™) Dose Using 3.5 as a Multiplier

| If the last 1-Month Paliperidone Palmitate Extended-Release Injectable Suspension dose is about: | Initiate 3-month paliperidone palmitate extended-release injectable suspension at about the following dose: |
|---|---|
| 50 mg eq. | 175 mg eq. |
| 75 mg eq. | 263 mg eq. |
| 100 mg eq. | 350 mg eq. |
| 150 mg eq. | 525 mg eq. |

Conversion from the 39 mg 1-month paliperidone palmitate extended-release injectable suspension was not studied.

Following the initial 3-month paliperidone palmitate extended-release injectable suspension, 3-month paliperidone palmitate extended-release injectable suspension should be administered every 3 months. If needed, dose adjustment can be made every 3 months in increments within the range of 273 mg to 819 mg based on individual patient tolerability and/or efficacy. Due to the long-acting nature of 3-month paliperidone palmitate extended-release injectable suspension, the patient's response to an adjusted dose may not be apparent for several months.

Missed Doses

Dosing Window

Missing doses of 3-month paliperidone palmitate extended-release injectable suspension should be avoided. However, on exceptional occasions, patients may be given the injection up to about 2 weeks before or after the 3-month time point.

Missed Dose >3½ Months and <4 Months Since Last Injection

If more than 3½ months (up to but less than 4 months) have elapsed since the last injection of 3-month paliperidone palmitate extended-release injectable suspension, the previously administered 3-month paliperidone palmitate extended-release injectable suspension dose should be administered as soon as possible, then continue with the 3-month injections following this dose.

Missed Dose Greater than or Equal to 4 Months Up to 9 Months Since Last Injection If between 4 to 9 months have elapsed since the last injection of 3-month paliperidone palmitate extended-release injectable suspension, do NOT administer the next dose of 3-month paliperidone palmitate extended-release injectable suspension. Instead, use the re-initiation regimen shown in Table 2.

TABLE 2

Re-Initiation Regimen After Missing ≥4 months up to 9 Months of 3-Month Extended-Release Injectable Suspension Dose

| Last 3-Month Extended Release Injectable Suspension dose | Administer PP1M, two doses one week apart (into deltoid muscle) | | Then administer 3-Month Extended Release Injectable Suspension Dose (into deltoid[a] or gluteal muscle) |
|---|---|---|---|
| | Day 1 | Day 8 | 1 month after day 8 |
| 175 mg eq. | 50 mg eq. → | 50 mg eq. → | 175 mg eq. |
| 263 mg eq. | 75 mg eq. → | 75 mg eq. → | 263 mg eq. |
| 350 mg eq. | 100 mg eq. → | 100 mg eq. → | 350 mg eq. |
| 525 mg eq. | 100 mg eq. → | 100 mg eq. → | 525 mg eq. |

[a] See Instructions for Use for deltoid injection needle selection based on body weight.

Missed Dose >9 Months Since Last Injection

If more than 9 months have elapsed since the last injection of 3-month paliperidone palmitate extended-release injectable suspension, re-initiate treatment with the 1-month paliperidone palmitate extended-release injectable suspension as described in the prescribing information for that product. 3-month paliperidone palmitate extended-release injectable suspension can then be resumed after the patient has been adequately treated with the 1-month paliperidone palmitate extended-release injectable suspension for at least 4 months.

1-Month Paliperidone Palmitate Extended-Release Injectable Suspension Dosing

The published US drug label for INVEGA SUSTENNA® 1-month paliperidone palmitate extended-release injectable suspension provides the appropriate dosing instructions for such product at various doses. This dosing regimen is also generally described in U.S. Patent Application No.

20090163519 for treating a psychiatric patient using paliperidone as a paliperidone palmitate ester in 1-month sustained release formulation. To attain a therapeutic plasma level of paliperidone, patients are administered to receive a first dose of paliperidone palmitate on day 1 of treatment, followed by a second dose between days 4 to 12 (and preferably about day 6 to 10) of treatment, then a third dose between days 29 to about 43 (and preferably from about 33 to about 39) of starting treatment. It is preferred that the patients will be administered the first dose on day 1, the second dose on day 8 after the first dose and the third dose on day 36 of after the first dose. The first two doses should be injected in the deltoid muscle. Thereafter paliperidone palmitate may be administered by injection approximately once a month (e.g. once every four weeks). To assure a potential therapeutic plasma level of paliperidone is attained, at least the first loading dose of about 150 mg-eq. of paliperidone as a paliperidone palmitate ester may be administered on day 1 of treatment. To further assure a potential therapeutic plasma level of paliperidone is attained by the patient, the first loading dose and the second loading dose ranging between from about 100 mg-eq. to about 150 mg-eq. of paliperidone as a paliperidone palmitate ester may be administered. To maintain a therapeutic level in the plasma, the subsequent doses thereafter or the maintenance dose ranging from about 25 mg-eq. to 150 mg-eq. per month may be administered. The maintenance dose may be administered intramuscularly into the deltoid or gluteal muscle, and the gluteal muscle is preferred. Those of ordinary skill in the art will understand that the maintenance dose may be titrated up or down in view of the patients' conditions such as response to the medication and renal function.

The models have indicated that there may be flexibility in the duration of the second loading dose and the maintenance dose of the maintenance dosing regimen for the 1-month paliperidone palmitate extended-release injectable suspension. For example, the second loading dose may be administered within the duration of about the $8^{th}$ day±4 days (or about 1 week±4 days) after administering of the first loading dose. Therefore, the second loading dose may be administered from about the $4^{th}$ to about the $12^{th}$ day after the first loading dose of the initial dosing. Similarly, the maintenance dose may be administered within the duration of about the $30^{th}$ day±7 days after administering of the first loading dose. Therefore, the maintenance dose may be administered from about the $23^{rd}$ day to about the $37^{th}$ day after administering of the second loading dose of the initial dosing. The flexible administration timing provides additional treatment benefit for patients who may require earlier administration or have missed their dose, within a short window, of the scheduled treatment without affecting the treatment effectiveness.

The models or simulations also indicate that 1-month paliperidone palmitate extended-release injectable suspension may be administered by intramuscular injection into either deltoid or gluteal muscle. The first and second loading dose of the initiation regimen may be administered in the deltoid muscle and the maintenance dose of the maintenance regimen may be administered in either the deltoid or gluteal muscle. The injection into the deltoid muscle may be delivered by a 1-inch 23-Gauge (G) or 1.5-inch 22-G needle based on the patient's weight. For the patients whose body weights are less than about 90 kg or 200 lb, a 1-inch 23-G needle may be used for administration, and for those body weights are equal or more than about 90 kg or 200 lb, a 1.5-inch 22-G needle may be used for administration. The injection into the gluteal muscle may be delivered by a 1.5-inch 22-G needle for all body weights.

By way of example, a dosing regimen is provided to switch patients from other injectable antipsychotic drug to 1-month paliperidone palmitate extended-release injectable suspension comprising administering into the deltoid muscle the initial dosing regimen comprising a first loading dose of about 234 mg of paliperidone palmitate and administering into the deltoid or gluteal muscle the maintenance regimen comprising a monthly maintenance dose of about 39 to about 234 mg of paliperidone palmitate on about the $23^{rd}$ day to about the $37^{th}$ day after administering of the first loading dose.

For patients who have previously received oral antipsychotic drugs, a switching treatment to 1-month paliperidone palmitate extended-release injectable suspension may comprise an initial dosing regimen and a monthly dosing regimen. The initial dosing regimen may comprise administering a first loading dose of 1-month paliperidone palmitate and administering a second loading dose of 1-month paliperidone palmitate, and the maintenance dosing regimen may comprise administering a maintenance dose of 1-month paliperidone palmitate. The previous oral antipsychotics may be discontinued at the time of initiation of the switching treatment or administration of the first loading dosing of 1-month paliperidone palmitate.

The monthly maintenance dose may be determined based on the condition of the patient and/or the severity of the disease. The preferred first loading dose may range from about 156 mg to about 234 mg of paliperidone palmitate, and more preferably about 234 mg. The preferred second loading dose may range from about 78 mg to about 156 mg, and more preferably about 156 mg. The preferred monthly maintenance dose may range from about 39 to about 234 mg, and more preferably about 117 mg. Subsequently, based on the patient tolerability and/or the drug efficacy, the maintenance dose may be further adjusted monthly to achieve optimal treatment effectiveness. The patients may be monitored for several months to ensure the full effect of the dose adjustment because of the prolonged-release characteristic of paliperidone palmitate.

Based on the pharmacokinetic simulations, patients previously stabilized on paliperidone in oral tablets may attain similar paliperidone steady-state exposure during maintenance treatment with paliperidone palmitate intramuscular injection monthly. For example, patients stabilized on oral paliperidone of about 3 mg may attain similar paliperidone steady-state exposure with the intramuscular injection of paliperidone palmitate of about 39 mg to about 78 mg. Similarly, patients stabilized on oral paliperidone of about 6 mg and about 12 mg may attain similar paliperidone steady-state exposure with the intramuscular injection of paliperidone palmitate of about 117 mg and about 234 mg, respectively. Therefore, during the maintenance regimen, the patients previously stabilized on paliperidone in oral tablets may be administered with the appropriate dose of paliperidone palmitate in injectable formulation corresponding to the stabilized dose of oral paliperidone.

As used herein, the term "stabilized dose" refers to the dose which is to be administered according the established dosing regimen. Preferably, the stabilized dose may be the maintenance dose of the monthly maintenance dosing regimen prior to a missed dose.

Also used herein, the terms "the first loading dose of the reinitiation regimen", "the first dose of the reinitiation regimen", "the first reinitiation dose" or variant thereof refer to the dose to be administered on day 1 when patients return to treatment. Similarly, the terms "the second loading dose of the reinitiation regimen", "the second dose of the reinitiation regimen", "the second reinitiation dose" or variant thereof refer to the dose to be administered after a week after the treatment day 1; and the terms "the maintenance dose of the reinitiation regimen", "the reinitiation maintenance dose" or variant thereof refer to the dose to be administered monthly after the treatment day 8.

Extended-Release Injectable Suspension Formulations

Paliperidone esters are psychotic agents belonging to the chemical class of benzisoxazole derivatives, which contains a racemic mixture of (+)- and (−)-paliperidone, which are described in U.S. Pat. No. 5,254,556 (incorporated herein by reference). The chemical name for paliperidone palmitate is (±)-3-[2-[4-(6-fluoro-1,2-benzisoxazol-3-yl)-1-piperidinyl] ethyl]-6,7,8,9-tetrahydro-2-methyl-4-oxo-4H-pyrido[1,2-c] pyrimidin-9-yl hexadecanoate. The structural formula is:

Paliperidone esters may be formulated with pharmaceutical excipients into injectable dosage forms as described in U.S. Pat. Nos. 5,254,556 and 6,077,843 both of which are incorporated herein by reference. Injectable formulations may be formulated in aqueous carriers.

Suitable aqueous depot formulations are described in U.S. Pat. No. 6,077,843 which is incorporated herein by reference. The 3-month formulations would have an averages size of less than about 20 μm to about 3 μm. Preferably the particles would have an average particle size (d50) of from about 10 μm to about 3 μm; preferably about 9 μm to about 4 μm.

The 1-month aqueous formulation would preferably be a nano particle suspension of wherein the nano particles would be of an averages size of less than about 2,000 nm to about 100 nm. Preferably the nano particles would have an average particle size (d50) of from about 1,600 nm to about 400 nm and most preferably about 1,400 nm to about 900 nm. Preferably the d90 will be less than about 5,000 nm and more preferably less than about 4,400 nm.

As used herein, an effective average particle size (d50) of less than about 2,000 nm means that at least 50% of the particles have a diameter of less than about 2,000 nm when measured by art-known conventional techniques, such as sedimentation field flow fractionation, photon correlation spectroscopy or disk centrifugation. With reference to the effective average particle size, it is preferred that at least about 90%, e.g. about 5,000 nm. Most preferably, about 90% of the particles have a size of less than about 4,400 nm.

Suitable aqueous nanoparticle depot 1-month formulations are described in U.S. Pat. No. 6,555,544 which is incorporated herein by reference. In one embodiment of the present invention the formulation would comprise nanoparticles, a surfactant, a suspending agent, and optionally one or more additional ingredients selected from the group consisting of preservatives, buffers and an isotonizing agent.

Useful surface modifiers paliperidone palmitate formulations are believed to include those that physically adhere to the surface of the active agent but do not chemically bond thereto. Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants. Representative examples of excipients include gelatin, casein, lecithin (phosphatides), gum acacia, cholesterol, tragacanth, stearic acid, benzalkonium chloride, calcium stearate, glyceryl monostearate, cetostearyl alcohol, cetomacrogol emulsifying wax, sorbitan esters, polyoxyethylene alkyl ethers, e.g., macrogol ethers such as cetomacrogol 1000, polyoxyethylene castor oil derivatives, polyoxyethylene sorbitan fatty acid esters, e.g., the commercially available TWEENS™, polyethylene glycols, polyoxyethylene stearates, colloidal silicon dioxide, phosphates, sodium dodecyl sulfate, carboxymethylcellulose calcium, carboxymethylcellulose sodium, methylcellulose, hydroxyethylcellulose, hydroxypropylcellulose, hydroxypropylmethylcellulose phtalate, noncrystalline cellulose, magnesium aluminate silicate, triethanolamine, polyvinyl alcohol (PVA), poloxamers, tyloxapol and polyvinylpyrrolidone (PVP). Most of these excipients are described in detail in the Handbook of Pharmaceutical Excipients, published jointly by the American Pharmaceutical Association and The Pharmaceutical Society of Great Britain, the Pharmaceutical Press, 1986. The surface modifiers are commercially available and/or can be prepared by techniques known in the art. Two or more surface modifiers can be used in combination.

Particularly preferred surface modifiers include polyvinylpyrrolidone; tyloxapol; poloxamers, such as PLURONIC™ F68, F108 and F127 which are block copolymers of ethylene oxide and propylene oxide available from BASF; poloxamines, such as TETRONIC™ 908 (T908) which is a tetrafunctional block copolymer derived from sequential addition of ethylene oxide and propylene oxide to ethylenediamine available from BASF; dextran; lecithin; Aerosol OT™ (AOT) which is a dioctyl ester of sodium sulfosuccinic acid available from Cytec Industries; DUPONOL™ P which is a sodium lauryl sulfate available from DuPont; TRITON™ X-200 which is an alkyl aryl polyether sulfonate available from Rohm and Haas; TWEEN™ 20, 40, 60 and 80 which are polyoxyethylene sorbitan fatty acid esters available from ICI Speciality Chemicals; SPAN™ 20, 40, 60 and 80 which are sorbitan esters of fatty acids; ARLACEL™ 20, 40, 60 and 80 which are sorbitan esters of fatty acids available from Hercules, Inc.; CARBOWAX™ 3550 and 934 which are polyethylene glycols available from Union Carbide; CRODESTA™ F110 which is a mixture of sucrose stearate and sucrose distearate available from Croda Inc.; CRODESTA™ SL-40 which is available from Croda, Inc.; hexyldecyl trimethyl ammonium chloride (CTAC); bovine serum albumin and SA90HCO which is $C_{18}H_{17}CH_2(CON(CH_3)CH_2(CHOH)_4CH_2OH)_2$. The surface modifiers which have been found to be particularly useful include tyloxapol and a poloxamer, preferably, Pluronic™ F108 and Pluronic™ F68.

Pluronic™ F108 corresponds to poloxamer 338 and is the polyoxyethylene, polyoxypropylene block copolymer that conforms generally to the formula $HO[CH_2CH_2O]_x[CH(CH_3)CH_2O]_y[CH_2CH_2O]_zH$ in which the average values of x, y and z are respectively 128, 54 and 128. Other commercial names of poloxamer 338 are Hodag NONIONIC™ 1108-F available from Hodag, and SYNPERONIC™ PE/F108 available from ICI Americas.

The optimal relative amount of paliperidone palmitate and the surface modifier depends on various parameters. The optimal amount of the surface modifier can depend, for example, upon the particular surface modifier selected, the critical micelle concentration of the surface modifier if it forms micelles, the surface area of the antipsychotic agent, etc. The specific surface modifier preferably is present in an amount of about 0.1 to about 1 mg per square meter surface area of the paliperidone palmitate. It is preferred in the case of paliperidone palmitate (9-hydroxyrisperidone palmitate) to use PLURONIC™ F108 as a surface modifier, a relative amount (w/w) of both ingredients of approximately 6:1 is preferred.

The particles of this invention can be prepared by a method comprising the steps of dispersing paliperidone palmitate in a liquid dispersion medium and applying mechanical means in the presence of grinding media to reduce the particle size of the antipsychotic agent to an effective average particle size. The particles can be reduced in size in the presence of a surface modifier. Alternatively, the particles can be contacted with a surface modifier after attrition.

A general procedure for preparing the particles for the 1-month formulation described herein includes (a) obtaining paliperidone palmitate in micronized form; (b) adding the micronized paliperidone palmitate to a liquid medium to form a premix; and (c) subjecting the premix to mechanical means in the presence of a grinding medium to reduce the effective average particle size.

The paliperidone palmitate in micronized form may be prepared using techniques known in the art. It is preferred that the particle size of the micronized paliperidone palmitate be less than about 100 µm as determined by sieve analysis. If the particle size of the micronized paliperidone palmitate is greater than about 100 µm, then it is preferred that the particles of paliperidone palmitate be reduced in size to less than 100 µm.

The micronized paliperidone palmitate can then be added to a liquid medium in which it is essentially insoluble to form a premix. The concentration of paliperidone palmitate in the liquid medium (weight by weight percentage) can vary widely and depends on the selected antipsychotic agent, the selected surface modifier and other factors. Suitable concentrations of paliperidone palmitate in compositions vary from about 0.1% to about 60%, preferably is from about 0.5% to about 30%, and more preferably, is approximately 7% (w/v). It is currently preferred to use a concentration of about 100 mg eq of paliperidone per ml or about 156 mg of paliperidone palmitate per ml.

A more preferred procedure involves the addition of a surface modifier to the premix prior to its subjection to mechanical means to reduce the effective average particle size. The concentration of the surface modifier (weight by weight percentage) can vary from about 0.1% to about 90%, preferably from about 0.5% to about 80%, and more preferably is approximately 7% (w/v).

The premix can be used directly by subjecting it to mechanical means to reduce the effective average particle size in the dispersion to less than about 2,000 nm. It is preferred that the premix be used directly when a ball mill is used for attrition. Alternatively, the antipsychotic agent and, optionally, the surface modifier, can be dispersed in the liquid medium using suitable agitation such as, for example, a roller mill or a Cowles type mixer, until a homogeneous dispersion is achieved.

The mechanical means applied to reduce the effective average particle size of the antipsychotic conveniently can take the form of a dispersion mill. Suitable dispersion mills include a ball mill, an attritor mill, a vibratory mill, a planetary mill, media mills—such as a sand mill and a bead mill. A media mill is preferred due to the relatively shorter milling time required to provide the desired reduction in particle size. For media milling, the apparent viscosity of the premix preferably is anywhere between about 0.1 Pa·s and about 1 Pa·s. For ball milling, the apparent viscosity of the premix preferably is anywhere between about 1 mPa·s and about 100 mPa·s.

The grinding media for the particle size reduction step can be selected from rigid media preferably spherical or particulate in form having an average size less than about 3 mm and, more preferably, less than about 1 mm. Such media desirably can provide the particles of the invention with shorter processing times and impart less wear to the milling equipment. The selection of the material for the grinding media is believed not to be critical. However, about 95% ZrO stabilized with magnesia, zirconium silicate, and glass grinding media provide particles which are acceptable for the preparation of pharmaceutical compositions. Further, other media, such as polymeric beads, stainless steel, titania, alumina and about 95% ZrO stabilized with yttrium, are useful. Preferred grinding media have a density greater than about 2.5 g/cm$^3$ and include about 95% ZrO stabilized with magnesia and polymeric beads.

The attrition time can vary widely and depends primarily upon the particular mechanical means and processing conditions selected. For rolling mills, processing times of up to two days or longer may be required for smaller size particles.

The particles must be reduced in size at a temperature which does not significantly degrade the antipsychotic agent. Processing temperatures of less than about 30° C. to about 40° C. are ordinarily preferred. If desired, the processing equipment may be cooled with conventional cooling equipment. The method is conveniently carried out under conditions of ambient temperature and at processing pressures which are safe and effective for the milling process.

The surface modifier, if it was not present in the premix, must be added to the dispersion after attrition in an amount as described for the premix above. Thereafter, the dispersion can be mixed by, for example, shaking vigorously. Optionally, the dispersion can be subjected to a sonication step using, for example, an ultrasonic power supply.

Aqueous compositions according to the present invention conveniently further comprise a suspending agent and a buffer, and optionally one or more of a preservative and an isotonizing agent. Particular ingredients may function as two or more of these agents simultaneously, e.g. behave like a preservative and a buffer, or behave like a buffer and an isotonizing agent.

Suitable suspending agents for use in the aqueous suspensions according to the present invention are cellulose derivatives, e.g. methyl cellulose, sodium carboxymethyl cellulose and hydroxypropyl methyl cellulose, polyvinylpyrrolidone, alginates, chitosan, dextrans, gelatin, polyethylene glycols, polyoxyethylene- and polyoxy-propylene ethers. Preferably sodium carboxymethyl cellulose is used in a concentration of about 0.5 to about 2%, most preferably about 1% (w/v).

Suitable wetting agents preferred from the listed surfactant for use in the aqueous suspensions according to the present invention are polyoxyethylene derivatives of sorbitan esters, e.g. polysorbate 20 and polysorbate 80, lecithin, polyoxyethylene- and polyoxypropylene ethers, sodium deoxycholate. Preferably polysorbate 20 is used in a concentration of about 0.5% to about 3%, more preferably about 0.5% to about 2%, most preferably about 1.1% (w/v).

Suitable buffering agents are salt of weak acids and should be used in amount sufficient to render the dispersion neutral to very slightly basic (up to the pH value of about 8.5), preferably in the pH range of about 7 to about 7.5. Particularly preferred is the use of a mixture of disodium hydrogen phosphate (anhydrous) (typically about 0.9% (w/v)) and sodium dihydrogen phosphate monohydrate (typically about 0.6% (w/v)). This buffer also renders the dispersion isotonic and, in addition, less prone to flocculation of the ester suspended therein.

Preservatives are antimicrobials and anti-oxidants which can be selected from the group consisting of benzoic acid, benzyl alcohol, butylated hydroxyanisole, butylated hydroxytoluene, chlorbutol, a gallate, a hydroxybenzoate, EDTA, phenol, chlorocresol, metacresol, benzethonium chloride, myristyl-gamma-piccolinium chloride, phenylmercuric acetate and thimerosal. In particular, it is benzyl alcohol which can be used in a concentration up to about 2% (w/v), preferably up to about 1.5% (w/v).

Isotonizing agents are, for example, sodium chloride, dextrose, mannitol, sorbitol, lactose, sodium sulfate. The suspensions conveniently comprise from about 0% to about 10% (w/v) isotonizing agent. Mannitol may be used in a concentration from about 0% to about 7% more preferably, however, from about 1% to about 3% (w/v), especially from about 1.5% to about 2% (w/v) of one or more electrolytes are used to render the suspension isotonic, apparently because ions help to prevent flocculation of the suspended ester. In particular, electrolytes of the buffer serve as isotonizing agent.

A particularly desirable feature for an injectable depot formulation relates to the ease with which it can be administered. In particular such an injection should be feasible using a needle as fine as possible in a span of time which is as short as possible. This can be accomplished with the aqueous suspensions of the present invention by keeping the viscosity below about 75 mPa·s, preferably below about 60 mPa·s. Aqueous suspensions of such viscosity or lower can both easily be taken up in a syringe (e.g. from a vial), and injected through a fine needle (e.g. a 21G 1½ inch, 22G 2 inch, 22G 1¼ inch or 23G 1 inch needle). The preferred needles for injection are 22G 22G 1½ inch regular wall and 23G 1 inch regular wall needles.

Ideally, aqueous suspensions according to the present invention will comprise as much prodrug as can be tolerated so as to keep the injected volume to a minimum, and as little of the other ingredients as possible. In particular for the 3-month formulation the composition will be (a) from about 280 to about 350 mg/mL of prodrug; (b) from about 8 to about 12 mg/mL of wetting agent; (c) from about 16 to about 22 mg/mL of one or more buffering agents to render the neutral to very slightly basic (pH 8.5); (d) from about 65 to about 85 mg/mL of a suspending agent; (e) up to about 2% (w/v) preservatives; and (f) water q.s. ad 100%. Most preferably the inactive ingredients in the 3-month formulation will be polysorbate 20 (about 10 mg/mL), polyethylene glycol 4000 (about 75 mg/mL), citric acid monohydrate (about 7.5 mg/mL), sodium dihydrogen phosphate monohydrate (about 6 mg/mL), sodium hydroxide (about 5.4 mg/mL) and water for injection. In particular, such a composition for the 1-month formulation will comprise by weight based on the total volume of the composition: (a) from about 3% to 20% (w/v) of the prodrug; (b) from about 0.5% to 2% (w/v) of a wetting agent; (c) one or more buffering agents sufficient to render the composition neutral to very slightly basic (pH 8.5); (d) from about 0.5% to about 2% (w/v) of a suspending agent; (e) up to about 2% (w/v) preservatives; and (f) water q.s. ad 100%. Preferably the aqueous suspension will be made under sterile conditions and no preservatives will be used. Appropriate methods to aseptically prepare paliperidone palmitate are described in WO 2006/114384 which is hereby incorporated by reference herein.

The preferred aqueous dosage form contains inactive ingredients that are polysorbate 20, polyethylene glycol 4000, citric acid monohydrate, disodium hydrogen phosphate anhydrous, sodium dihydrogen phosphate monohydrate, sodium hydroxide, and water for injection.

As used herein, a dose or dosing is expressed as milligrams (mg) of paliperidone palmitate. Paliperidone palmitate dosing may also be expressed as mg equivalents (mg eq.) of paliperidone with about 39, 78, 117, 156, and 234 mg of paliperidone palmitate being equivalent to about 25, 50, 75, 100 and 150 mg eq., of paliperidone, respectively. For three month depot dosing it is preferred to dose patients with about 175 mg eq. to about 525 mg eq. paliperidone or about 273 mg to about 819 mg paliperidone palmitate.

The term "antipsychotics" or "antipsychotic drug medication" as used herein means any medication used to decrease or ameliorate the symptoms of psychosis in a person with a psychotic disorder.

The term "psychiatric patient" as used herein, refers to a human, who has been the object of treatment, or experiment for a "mental disorder" and "mental illness" refer to those provided in the Diagnostic and Statistical Manual (DSM IV), American Psychological Association (APA). Those of ordinary skill in the art will appreciate that paliperidone esters (e.g. paliperidone palmitate) can be administered to psychiatric patients for all the known uses of risperidone. These mental disorders include, but are not limited to, schizophrenia; bipolar disorder or other disease states in which psychosis, aggressive behavior, anxiety or depression is evidenced. Schizophrenia refers to conditions characterized as schizophrenia, schizoaffective disorder and schizophreniform disorders, in DSM-IV-TR such as category 295.xx. Bipolar Disorder refers to a condition characterized as a Bipolar Disorder, in DSM-IV-TR such as category 296.xx including Bipolar I and Bipolar Disorder II. The DSM-IV-TR was prepared by the Task Force on Nomenclature and Statistics of the American Psychiatric Association, and provides clear descriptions of diagnostic categories. Pathologic psychological conditions, which are psychoses or may be associated with psychotic features include, but are not limited to the following disorders that have been characterized in the DSM-IV-TR. Diagnostic and Statistical Manual of Mental Disorders, Revised, 3rd Ed. (1994). The skilled artisan will recognize that there are alternative nomenclatures, nosologies, and classification systems for pathologic psychological conditions and that these systems evolve with medical scientific progress. Examples of pathologic psychological conditions which may be treated include, but are not limited to, Mild Mental Retardation (317), Moderate Mental Retardation (318.0), Severe Mental Retardation (318.1), Profound Mental Retardation (318.2), Mental Retardation Severity Unspecified (319), Autistic Disorders (299.00), Rett's Disorder (299.80), Childhood Disintegrative Disorders (299.10), Asperger's Disorder (299.80), Pervasive Developmental Disorder Not Otherwise Specified (299.80), Attention-Deficit/Hyperactivity Disorder Combined Type (314.01), Attention-Deficit/ Hyperactivity Disorder Predominately Inattentive Type (314.00), Attention-Deficit/Hyperactivity Disorder Predominately Hyperactive-Impulsive Type (314.01), Attention-Deficit/Hyperactivity Disorder NOS (314.9), Conduct Disorder (Childhood-Onset and Adolescent Type 312.8), Oppositional Defiant Disorder (313.81), Disruptive Behavior Disorder Not Otherwise Specified (312.9), Solitary Aggressive Type (312.00), Conduct Disorder, Undifferentiated Type (312.90), Tourette's Disorder (307.23), Chronic Motor Or Vocal Tic Disorder (307.22), Transient Tic Disorder (307.21), Tic Disorder NOS (307.20), Alcohol Intoxication Delirium (291.0), Alcohol Withdrawal Delirium (291.0), Alcohol-Induced Persisting Dementia (291.2), Alcohol-Induced Psychotic Disorder with Delusions (291.5), Alcohol-Induced Psychotic Disorder with Hallucinations (291.3), Amphetamine or Similarly Acting Sympathomimetic Intoxication (292.89), Amphetamine or Similarly Acting Sympathomimetic Delirium (292.81), Amphetamine or Similarly Acting Sympathomimetic Induced Psychotic with Delusions (292.11), Amphetamine or Similarly Acting Sympathomimetic Induced Psychotic with Hallucinations (292.12), Cannabis-Induced Psychotic Disorder with Delusions (292.11), Cannabis-Induced Psychotic Disorder with Hallucinations (292.12), Cocaine Intoxication (292.89), Cocaine Intoxication Delirium (292.81), Cocaine-Induced Psychotic Disorder with Delusions (292.11), Cocaine-Induced Psychotic Disorder with Hallucinations (292.12), Hallucinogen Intoxication (292.89), Hallucinogen Intoxication Delirium (292.81), Hallucinogen-Induced Psychotic disorder with Delusions (292.11), Hallucinogen-Induced Psychotic disorder with Delusions (292.12), Hallucinogen-Induced Mood Disorder (292.84), Hallucinogen-Induced Anxiety Disorder (292.89), Hallucinogen-Related Disorder Not Otherwise Specified (292.9), Inhalant Intoxication (292.89), Inhalant Intoxication Delirium (292.81), Inhalant-Induced Persisting Dementia (292.82), Inhalant-Induced Psychotic Disorder with Delusions (292.11), Inhalant-Induced Psychotic with Hallucinations (292.12), Inhalant-Induced Mood Disorder (292.89), Inhalant-Induced Anxiety Disorder (292.89), Inhalant-Related Disorder Not Otherwise Specified (292.9), Opioid Intoxication Delirium (292.81), Opioid-Induced Psychotic Disorder with Delusions (292.11), Opioid Intoxication Delirium (292.81), Opioid-Induced Psychotic Disorder with Hallucinations (292.12), Opioid-Induced Mood Disorder (292.84), Phencyclidine (PCP) or Similarly Acting Arylcyclohexylamine Intoxication (292.89), Phencyclidine (PCP) or Similarly Acting Arylcyclohexylamine Intoxication Delirium (292.81), Phencyclidine (PCP) or Similarly Acting Arylcyclohexylamine Induced Psychotic Disorder with Delusions (292.11), Phencyclidine (PCP) or Similarly Acting Arylcyclohexylamine Induced Psychotic Disorder with Hallucinations (292.12), Phencyclidine (PCP) or Similarly Acting Arylcyclohexylamine Mood Disorder (292.84), Phencyclidine (PCP) or Similarly Acting Arylcyclohexylamine Induced Anxiety Disorder (292.89), Phencyclidine (PCP) or Similarly Acting Arylcyclohexylamine Related Disorder Not Otherwise Specified (292.9), Sedative, Hypnotic or Anxiolytic Intoxication (292.89), Sedation, Hypnotic or Anxiolytic Intoxication Delirium (292.81), Sedation, Hypnotic or Anxiolytic Withdrawal Delirium (292.81), Sedation, Hypnotic or Anxiolytic Induced Persisting Dementia (292.82), Sedation, Hypnotic or Anxiolytic-Induced Psychotic Disorder with Delusions (292.11), Sedation, Hypnotic or Anxiolytic-Induced Psychotic Disorder with Hallucinations (292.12), Sedation, Hypnotic or Anxiolytic-Induced Mood Disorder (292.84), Sedation, Hypnotic or Anxiolytic-Induced Anxiety Disorder (292.89), Other (or Unknown) Substance Intoxication (292.89), Other (or Unknown) Substance-Induced Delirium (292.81), Other (or Unknown) Substance-Induced Persisting Dementia (292.82), Other (or Unknown) Substance-Induced Psychotic Disorder with Delusions (292.11), Other (or Unknown) Substance-Induced Psychotic Disorder with Hallucinations (292.12), Other (or Unknown) Substance-Induced Mood Disorder (292.84), Other (or Unknown) Substance-Induced Anxiety Disorder (292.89), Other (or Unknown) Substance Disorder Not Otherwise Specified (292.9), Obsessive Compulsive Disorder (300.3), Post-traumatic Stress Disorder (309.81), Generalized Anxiety Disorder (300.02), Anxiety Disorder Not Otherwise Specified (300.00), Body Dysmorphic Disorder (300.7), Hypochondriasis (or Hypochondriacal Neurosis) (300.7), Somatization Disorder (300.81), Undifferentiated Somatoform Disorder (300.81), Somatoform Disorder Not Otherwise Specified (300.81), Intermittent Explosive Disorder (312.34), Kleptomania (312.32), Pathological Gambling (312.31), Pyromania (312.33), Trichotillomania (312.39), and Impulse Control Disorder NOS (312.30), Schizophrenia, Paranoid Type, (295.30), Schizophrenia, Disorganized (295.10), Schizophrenia, Catatonic Type, (295.20), Schizophrenia, Undifferentiated Type (295.90), Schizophrenia, Residual Type (295.60), Schizophreniform Disorder (295.40), Schizoaffective Disorder (295.70), Delusional Disorder (297.1), Brief Psychotic Disorder (298.8), Shared Psychotic Disorder (297.3), Psychotic Disorder Due to a General Medical Condition with Delusions (293.81), Psychotic Disorder Due to a General Medical Condition with Hallucinations (293.82), Psychotic Disorders Not Otherwise Specified (298.9), Major Depression, Single Episode, Severe, without Psychotic Features (296.23), Major Depression, Recurrent, Severe, without Psychotic Features (296.33), Bipolar Disorder, Mixed, Severe, without Psychotic Features (296.63), Bipolar Disorder, Mixed, Severe, with Psychotic Features (296.64), Bipolar Disorder, Manic, Severe, without Psychotic Features (296.43), Bipolar Disorder, Manic, Severe, with Psychotic Features (296.44), Bipolar Disorder, Depressed, Severe, without Psychotic Features (296.53), Bipolar Disorder, Depressed, Severe, with Psychotic Features (296.54), Bipolar II Disorder (296.89), Bipolar Disorder Not Otherwise Specified (296.80), Personality Disorders, Paranoid (301.0), Personality Disorders, Schizoid (301.20), Personality Disorders, Schizotypal (301.22), Personality Disorders, Antisocial (301.7), and Personality Disorders, Borderline (301.83). The numbers in parenthesis refer to the DSM-IV-TR categories.

The term "therapeutically effective amount" as used herein, means that amount of active compound or pharmaceutical agent that elicits the biological or medicinal response in human that is being sought by a researcher, medical doctor or other clinician, which includes alleviation of the symptoms of the disease or disorder being treated.

Those of skill in the treatment of diseases could easily determine the effective amount of paliperidone to administer for the treatment of the diseases listed above. By way of example, an effective amount of paliperidone for the treatment of mental disorders would be from about 0.01 mg/kg to about 2 mg/kg body weight per day. For monthly depot dosing it is preferred to dose patients with about 25 mg-eq. to about 150 mg eq. paliperidone or about 39 mg to about 234 mg paliperidone palmitate. The amount of paliperidone palmitate is provided in sufficient amount to provide the equivalent dose of paliperidone after the palmitic acid moiety is removed from the ester (e.g. 156 mg corresponds to paliperidone 100 mg). For three month depot dosing it is preferred to dose patients with about 175 mg eq. to about 525 mg eq. paliperidone or about 273 mg to about 819 mg paliperidone palmitate.

TABLE 3

Conversion between mg PP and mg eq. paliperidone for PP1M and PP3M

| PP1M Dose (mg PP) | PP1M Dose (mg eq. Paliperidone) | PP3M Dose (mg PP) | PP3M Dose (mg eq. Paliperidone) |
|---|---|---|---|
| 78 mg | 50 mg eq. | 273 mg | 175 mg eq. |
| 117 mg | 75 mg eq. | 410 mg | 263 mg eq. |
| 156 mg | 100 mg eq. | 546 mg | 350 mg eq. |
| 234 mg | 150 mg eq. | 819 mg | 525 mg eq. |

PP, paliperidone palmitate;
PP3M, PP 3-month formulation;
PP1M, PP 1-month formulation.

The following non-limiting examples are provided to further illustrate the present invention.

Example 1. Methodology

Population Pharmacokinetics Models

A comprehensive population pharmacokinetics (PK) model was developed for paliperidone palmitate based on data from previous studies of subjects with schizophrenia. Briefly, a population PK model was developed, using the first-order conditional estimation method (FOCE), to estimate the population PK parameters of paliperidone after single and multiple dose administration of PP3M. The population PK model was constructed using data from a phase-I (NCT01559272) and phase-III study (NCT01529515). The final population PK model was based on 8990 PK samples from 651 patients.

The PP1M and PP3M models were one-compartment models with first-order elimination. In the PP1M absorption sub-model, a fraction of the dose entered the central compartment relatively quickly via a zero-order process. After a certain lag time, the remaining fraction of the dose entered the systemic circulation via a first-order process. The PP3M absorption sub-model consisted of 2 saturable absorption processes.

Model Based Simulations

The population PK model was used for simulating pre-defined dosing regimen scenarios. Paliperidone plasma concentrations were simulated based on the estimates of the final population PK model using profiles from 5000 patients. The patient population for simulation was built by sampling, with replacement of demographic data from patients in the data set used for the development of PP1M[4] and PP3M models. PK simulations were performed in NONMEM version 7.3.0 and data management/processing of NONMEM output was performed using R 3.0.2 (NONMEM User Guides, Icon Development solutions, Ellicott City, Md.). The population median and 90% prediction interval of the simulated plasma concentration-time profiles were plotted and graphically presented to evaluate the outcome.

Dosing Windows and Missed Doses

Simulations were performed to assess the dosing window during:
(i) switching from PP1M (150 or 50 mg eq.) to PP3M (525 or 175 mg eq.) at week 17 and with a ±1 week dosing window; and
(ii) maintenance therapy with PP3M (525 or 175 mg eq.) at regular week 12 and with a ±1 to 3 week dosing window The paliperidone plasma concentration—time profiles were also simulated for the missed dose scenarios when the third 525 mg eq. PP3M dose was missed and treatment was reinitiated depending on the duration since the last dose.

TABLE 4

Conversion between mg PP and mg eq. paliperidone for PP1M and PP3M

| PP1M Dose (mg PP) | PP1M Dose (mg eq. Paliperidone) | PP3M Dose (mg PP) | PP3M Dose (mg eq. Paliperidone) |
|---|---|---|---|
| 78 mg | 50 mg eq. | 273 mg | 175 mg eq. |
| 117 mg | 75 mg eq. | 410 mg | 263 mg eq. |
| 156 mg | 100 mg eq. | 546 mg | 350 mg eq. |
| 234 mg | 150 mg eq. | 819 mg | 525 mg eq. |

PP, paliperidone palmitate;
PP3M, PP 3-month formulation;
PP1M, PP 1-month formulation.

TABLE 5

Dosing reinitiation regimen for the missed dose simulations

| Time interval of missed dose | Reinitiation treatment |
|---|---|
| <4 months | Continue PP3M Q12W |
| 4-9 months | treatment reinitiated with 2 PP1M deltoid injections separated by one week, followed by PP3M dosing Q12W |
| >9 months | 150 mg eq. PP1M deltoid injection on day 1 and 100 mg eq. PP1M deltoid injection on day 8, followed by 3 additional PP1M injections, before continuing PP3M dosing Q12W |

Furthermore, paliperidone plasma concentrations versus time after stopping multiple PP3M doses were simulated.

Assessment of Q12W Vs Q13W

Finally, simulations were also performed to compare Q12W vs Q13W dosing at steady state with PP3M and to demonstrate the impact of actual 3 months dosing (13 weeks) on paliperidone levels.

Figure 1:
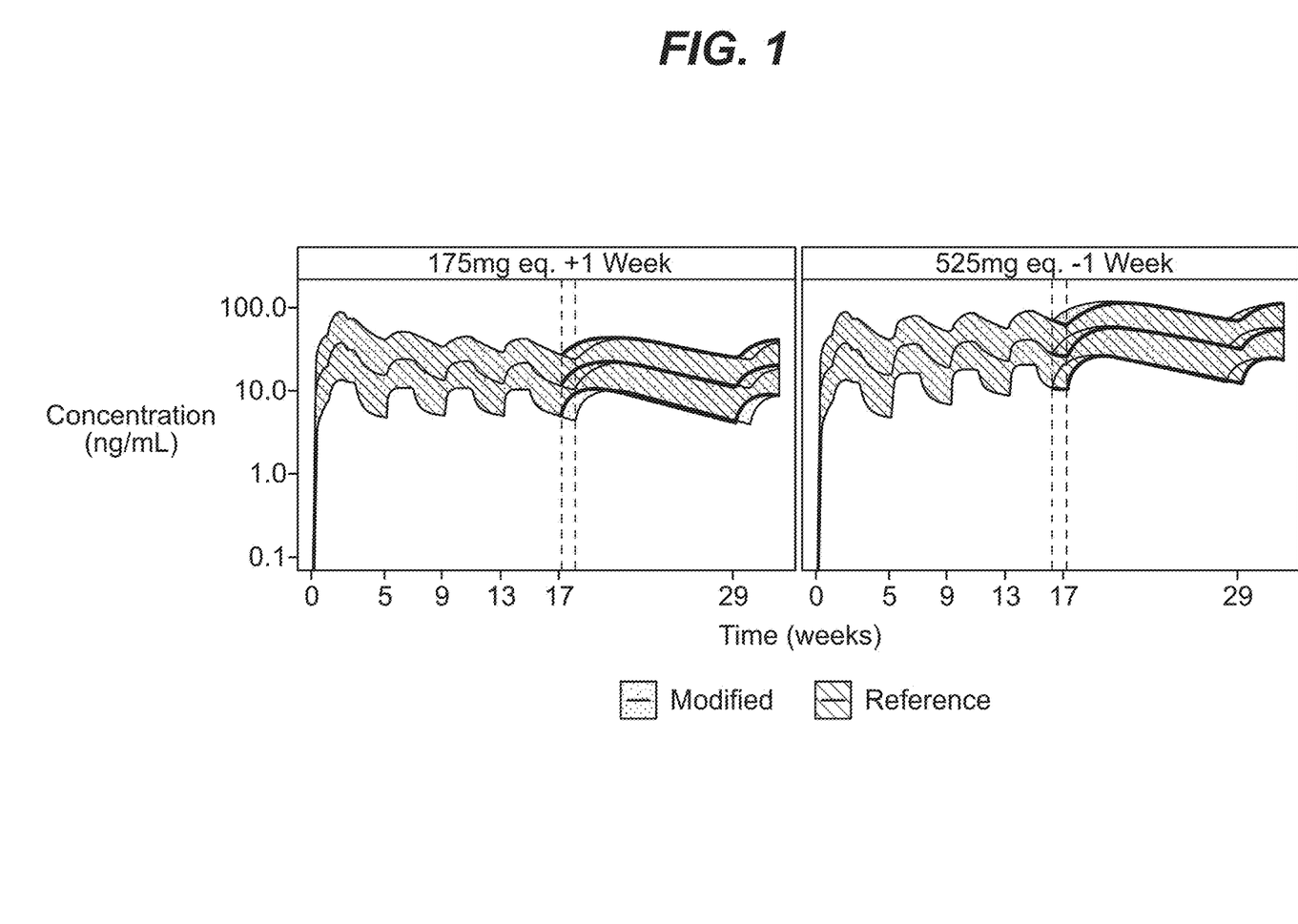
FIG. 1 illustrates the switching from PP1M to PP3M at default week 17±1 Week.

Results:

In FIG. 1 the switching from PP1M to PP3M at a default of week 17±1 week resulting in:

TABLE 6

| Window | | $C_{min}$ (ng/mL) |
|---|---|---|
| +1 week | Reference | 11.6 |
| 50 mg eq. PP1M Switched to 175 mg eq. PP3M dose | Modified | 10.2 |
| −1 week | Reference | 58.2 |
| 150 mg eq. PP1M Switched to 525 mg eq. PP3M dose | Modified | 60.2 |

As illustrated by FIG. 1 switching from 50 mg eq. PP1M to 175 mg eq. PP3M at Week 18 instead of Week 17 led to a decrease in $C_{min}$ from 11.6 ng/mL to 10.2 ng/mL, and switching from 150 mg eq. PP1M to 525 mg eq. PP3M at Week 16 instead of Week 17 led to an increase in $C_{max}$ from 58.2 ng/mL to 60.2 ng/mL. These changes in plasma concentrations are relatively small when a ±1 week window is allowed at the time of switching from PP1M to PP3M.

Figure 2A:
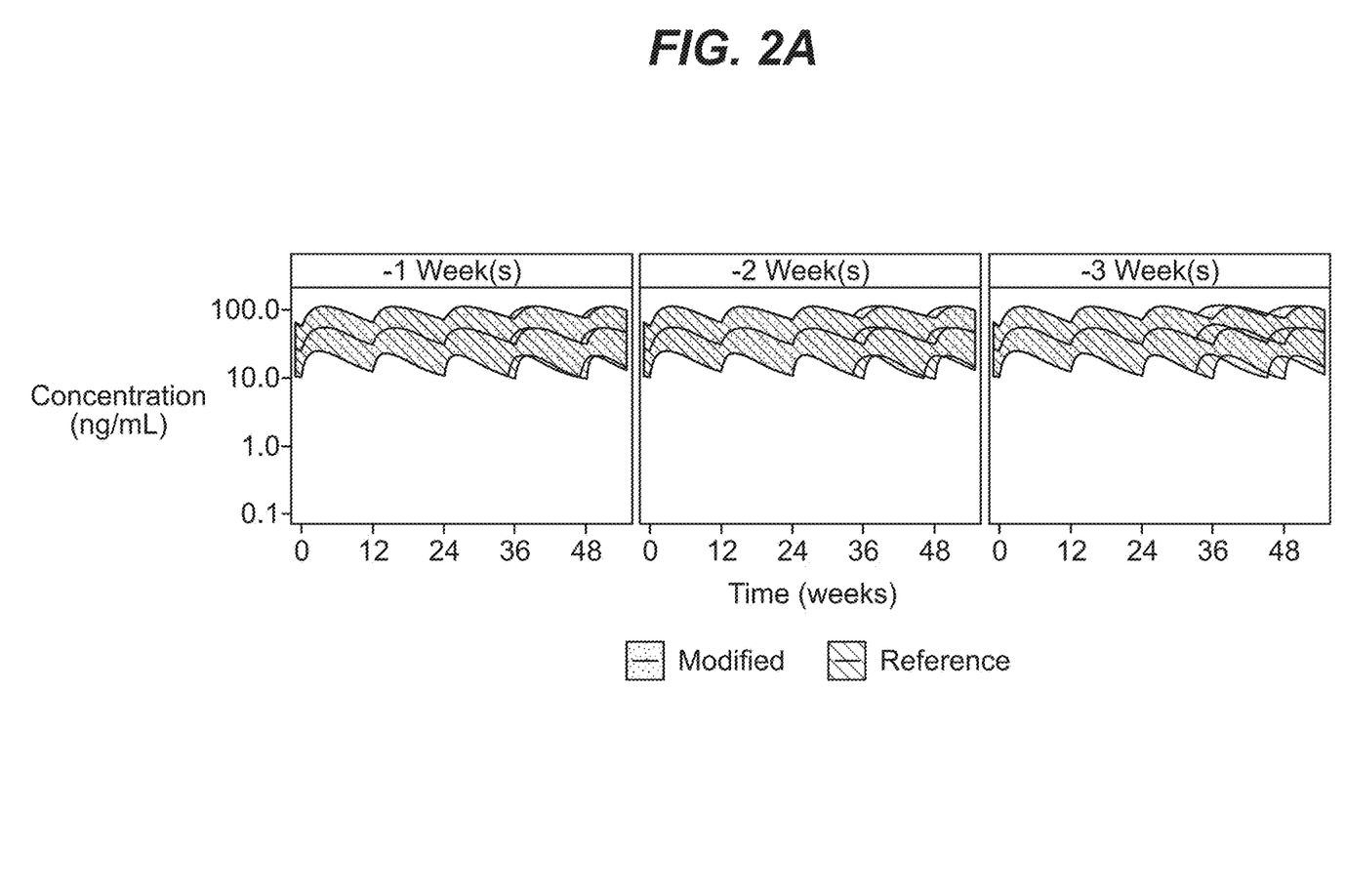
FIGS. 2A-2B illustrate the dosing windows around the regularly scheduled 12-week dosing interval. Graphs of modeled results of dosing before regularly scheduled injections of (A) 525 mg eq. PP3M (B) 175 mg eq. PP3M.
Figure 2B:
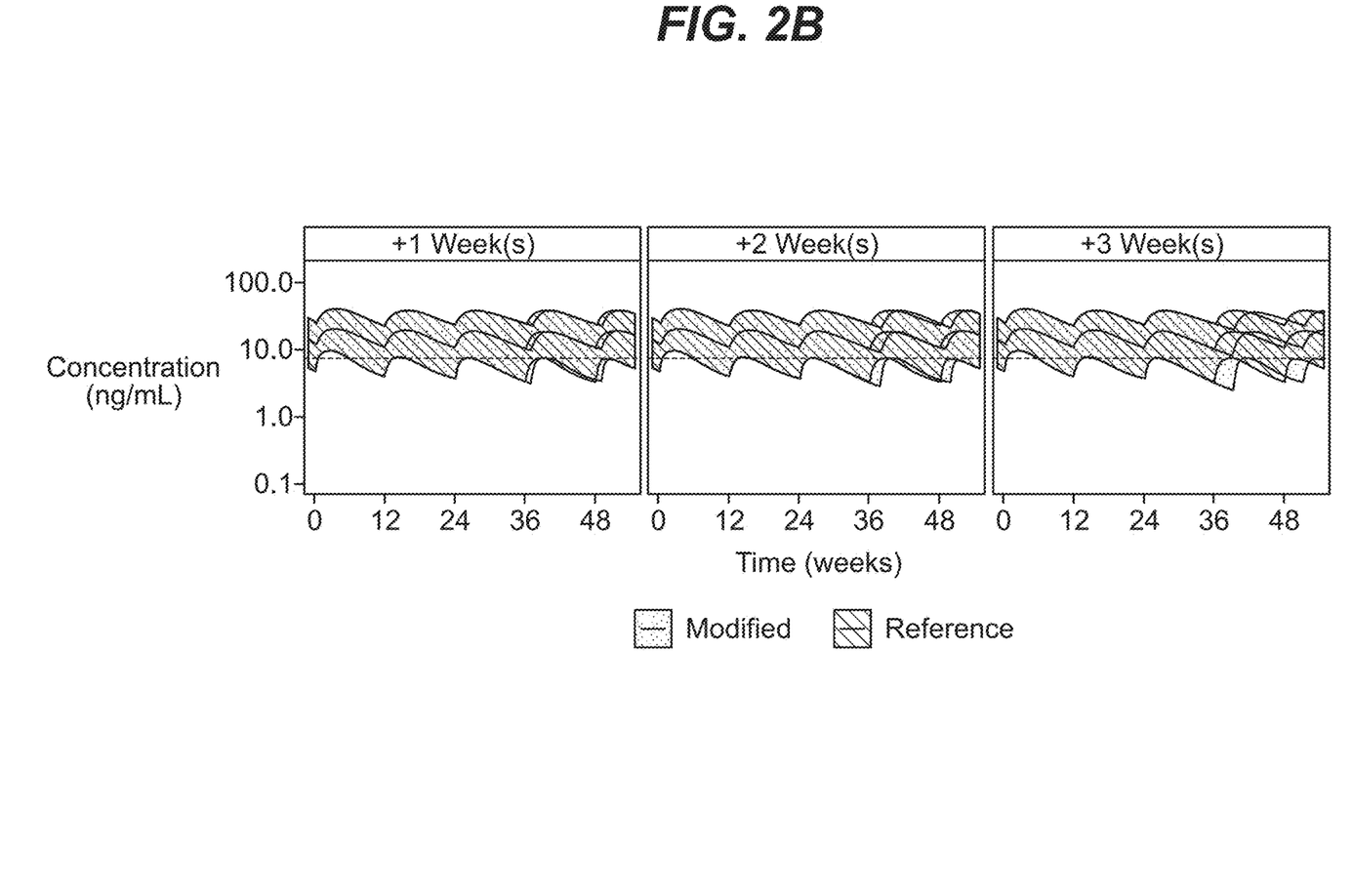
Figure 3:
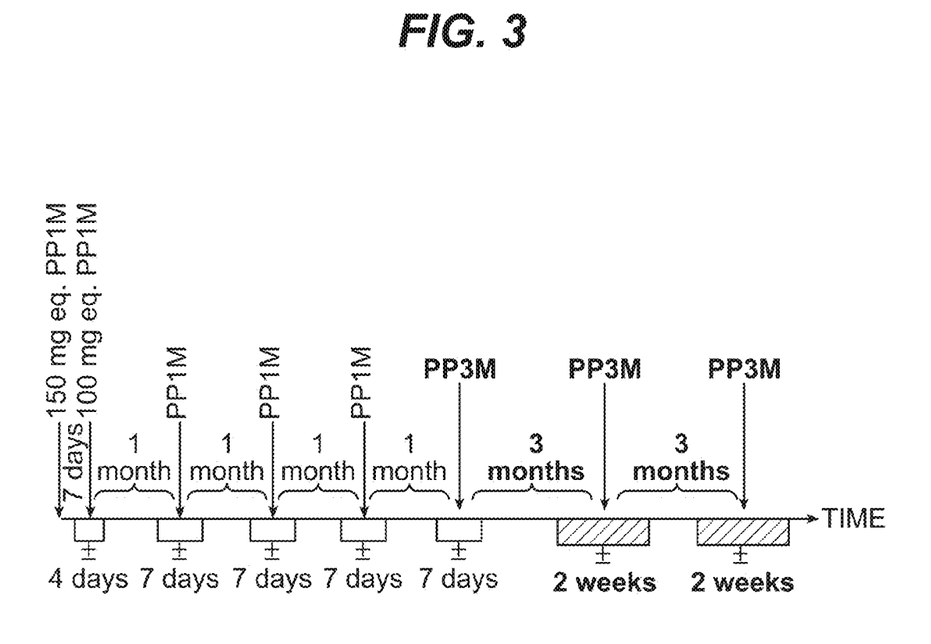
FIG. 3 illustrates the dosing windows for PP1M and PP3M dosing regimen.

In FIGS. 2A-2B the PP3M with a 12 week dosing week was modeled. In FIG. 2A the −X week simulations were performed with the highest PP3M dose strength of 525 mg eq. to simulate a worst-case scenario (i.e., largest % increase in Cmax).

TABLE 7

| 525 mg eq. PP3M | $C_{max}$ (ng/mL) |
| --- | --- |
| Reference | 56.4 |
| Modified (−1 week) | 57.1 |
| Modified (−2 week) | 58.0 |
| Modified (−3 week) | 58.8 |

In FIG. 2B) the +X week simulations were performed with the lowest PP3M dose strength of 175 mg eq. to simulate a worst-case scenario (i.e., largest % drop in Cmin) since the lowest dose has the shortest apparent t½.

TABLE 8

| 175 mg eq. PP3M | $C_{min}$ (ng/mL) |
| --- | --- |
| Reference | 11.0 |
| Modified (+1 week) | 10.3 |
| Modified (+2 week) | 9.7 |
| Modified (+3 week) | 9.0 |

After stabilization on PP3M, administration of 175 mg eq. PP3M:
 1 week later than the scheduled: Cmin decreased by 0.7 ng/mL
 2 weeks later than the scheduled: $C_{min}$ decreased by 1.3 ng/mL
 3 weeks later than the scheduled: $C_{min}$ decreased by 2.0 ng/mL After stabilization on PP3M, administration of 525 mg eq. PP3M,
 1 week earlier than scheduled: $C_{max}$ increased by 0.7 ng/mL
 2 weeks earlier than scheduled: $C_{max}$ increased by 1.6 ng/mL
 3 weeks earlier than scheduled: $C_{max}$ increased by 2.4 ng/mL FIG. 2B illustrates the simulations done with 12 weeks with a maximum possible window of +3 weeks. However, 3 months is 13 weeks hence the simulations illustrates 3 months+2 week window. These changes in plasma concentrations are relatively small and justify a ±3 week window for Q12W administration of PP3M, which corresponds to a ±2 week window for Q13W (i.e. every 3 months) administration.

Figure 4A:
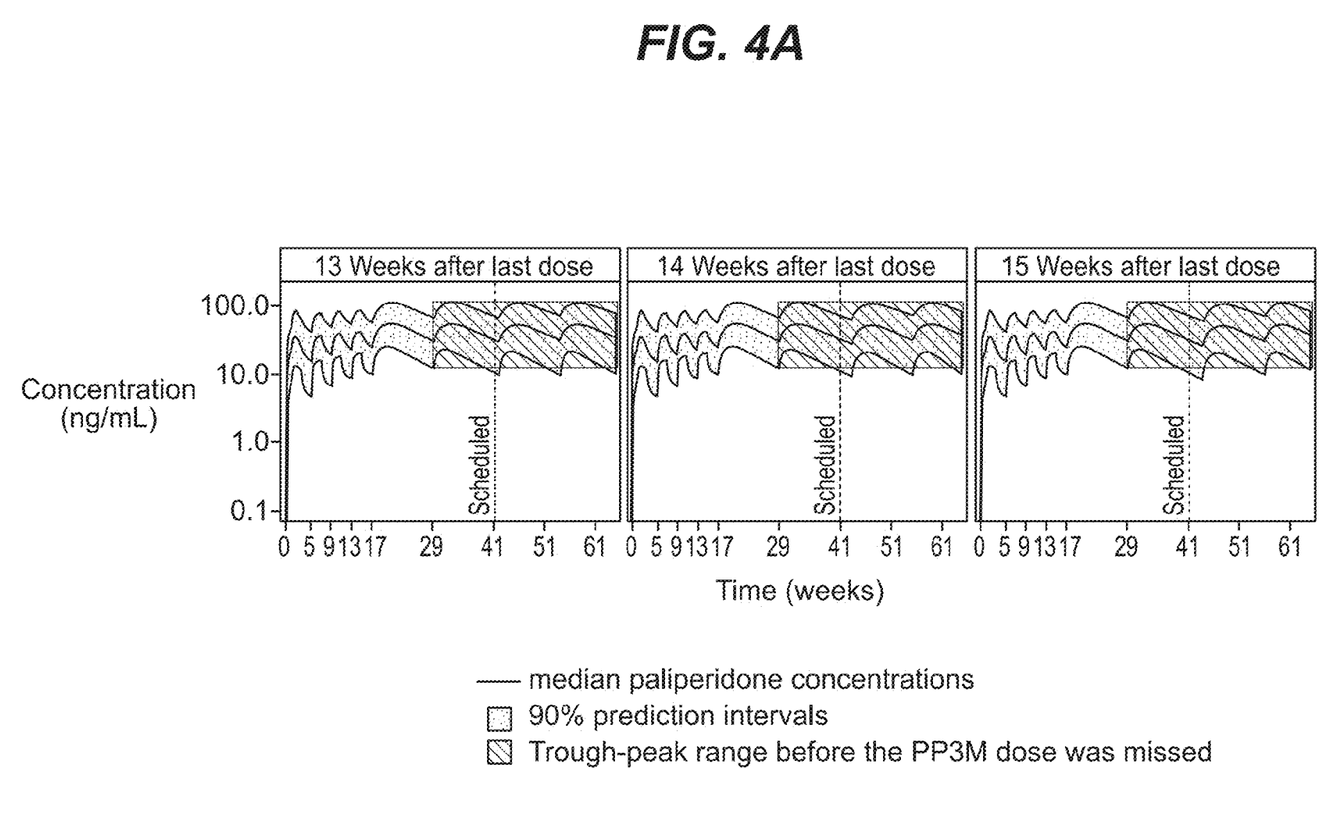
FIGS. 4A-4C illustrate predicted plasma concentration of PP3M (525 mg eq.). Graphs of modeled results of missed dosing for (A) <4 months. (B) between 4 to 9 months (C) >9 months.
Figure 4B:
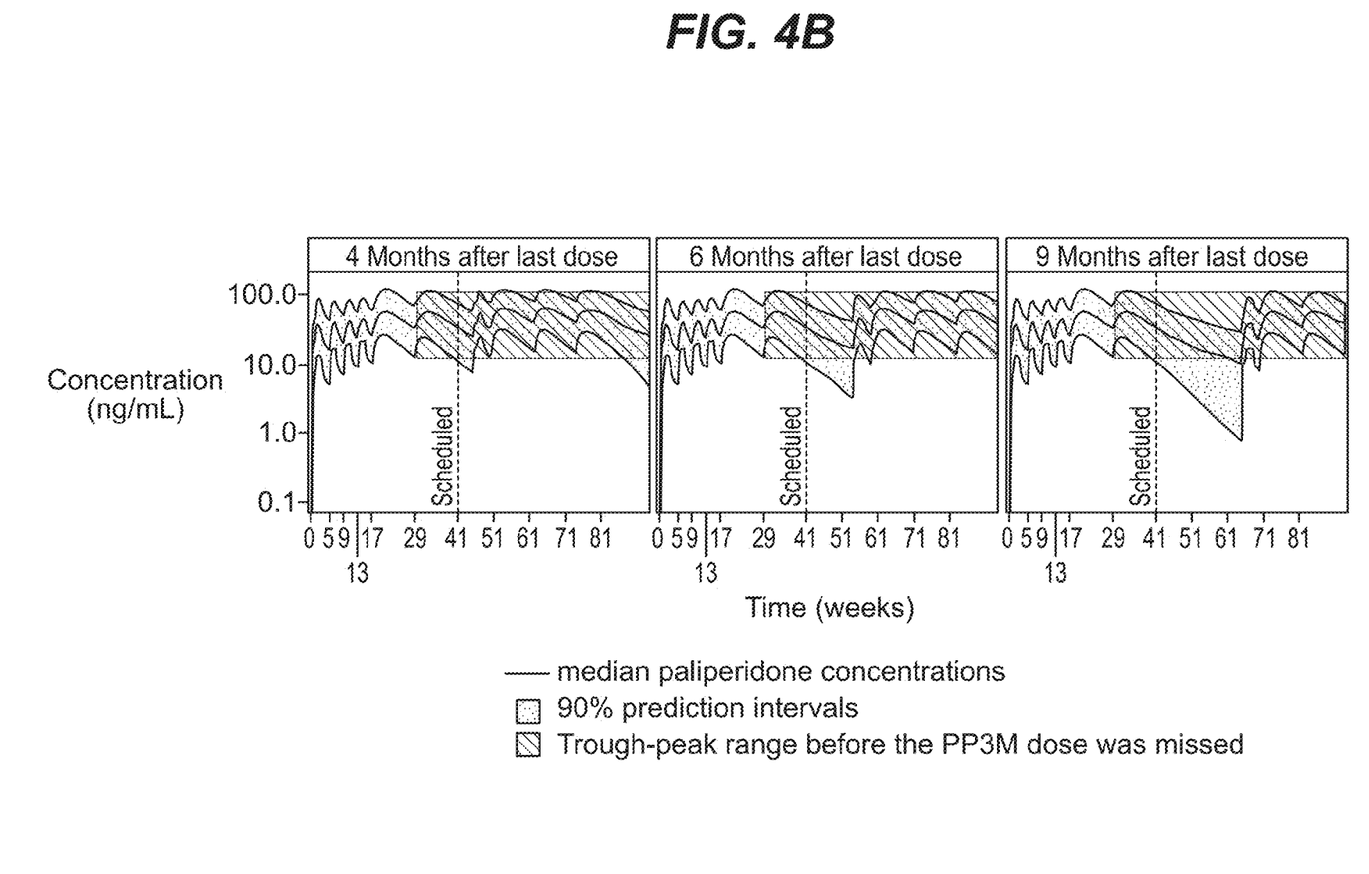
Figure 4C:
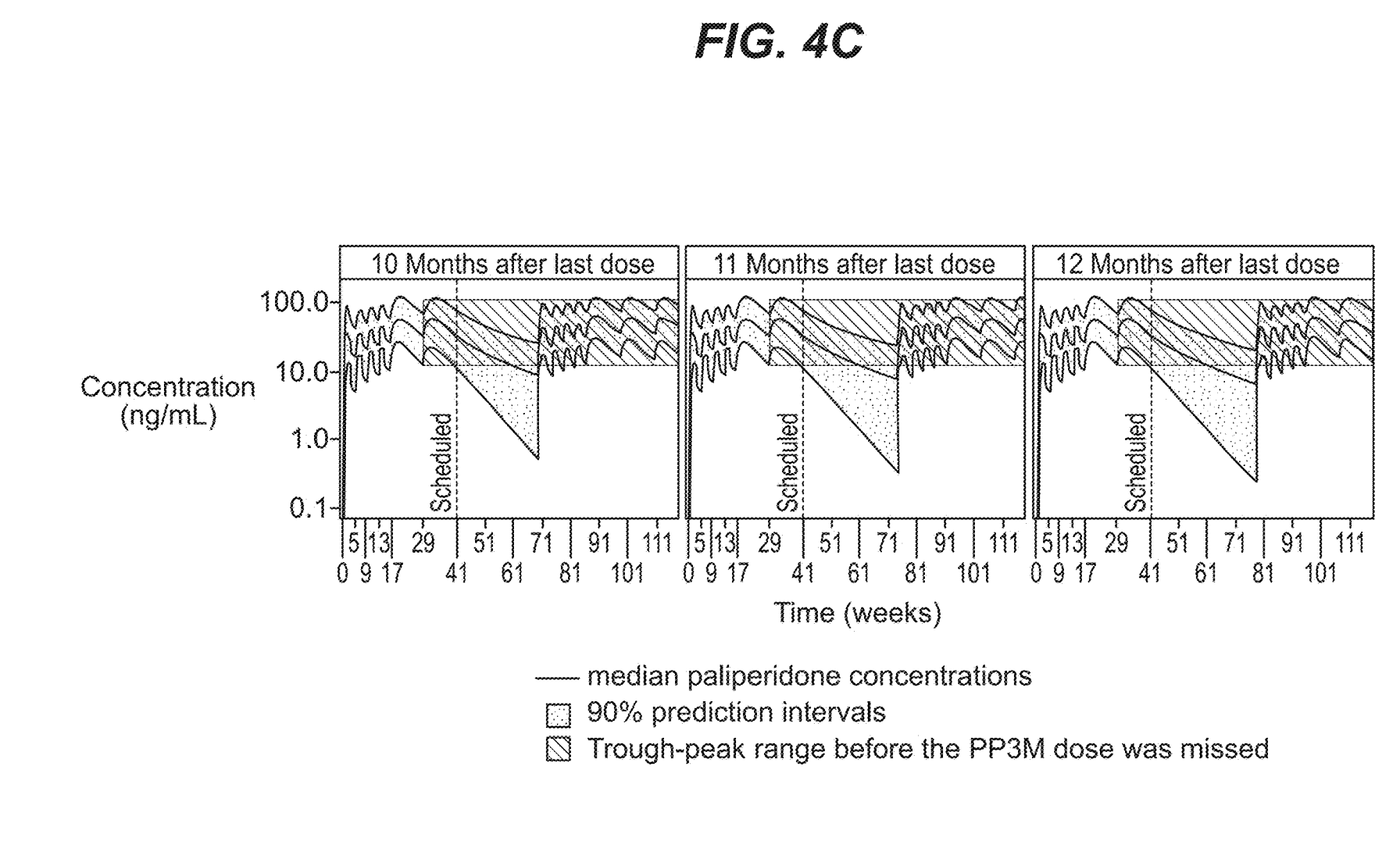

FIG. 4A-4C illustrate the predicted plasma concentration of PP3M (525 mg. eq.) at various time intervals. Similar paliperidone plasma outcomes were observed for other dosage strengths. Similar paliperidone plasma concentration as before the missed dose was achieved by the following reinitiation treatment:
 PP3M missed by <4 months, treatment reinitiated with regular PP3M injections
 PP3M missed between 4-9 months, treatment reinitiated with 2 PP1M deltoid injections separated by one week, followed by PP3M dosing Q12W using the regimen described in the table below:

TABLE 9

| Re-initiation regimen after missing ≥4 months up to 9 months of PP3M | | | |
| --- | --- | --- | --- |
| Last PP3M | Administer PP1M, two doses one week apart (into deltoid muscle) | | Then administer PP3M (into deltoid[a] or gluteal muscle) |
| dose | Day 1 | Day 8 | 1 month after day 8 |
| 175 mg eq. | 50 mg eq. → | 50 mg eq. → | 175 mg eq. |
| 263 mg eq. | 75 mg eq. → | 75 mg eq. → | 263 mg eq. |
| 350 mg eq. | 100 mg eq. → | 100 mg eq. → | 350 mg eq. |
| 525 mg eq. | 100 mg eq. → | 100 mg eq. → | 525 mg eq. |

PP3M missed for >9 months, treatment reinitiated with PP1M for 4 months before continuation of PP3M Q12W Concentration of ≥7.5 ng/mL was maintained up to 10 to 14 months after the discontinuation of 350 and 525 mg eq.PP3M.

Paliperidone concentration of 7.5 ng/mL is associated with 60% $D_2$ receptor occupancy, and is thought to be required for antipsychotic efficacy[5]. These simulations therefore support re-initiation with at least 4 months of treatment with PP1M (before transitioning to PP3M) if a maintenance dose of PP3M is missed for more than 9 months.

Additional simulations also showed a similar outcome with other dose strengths (data not shown).

What is claimed is:

1. A dosing regimen for administering an injectable paliperidone palmitate depot to a patient in need of treatment for psychosis, schizophrenia or bipolar disorder that has been treated with a 3-month injectable paliperidone palmitate depot (PP3M), wherein said patient had been last administered a PP3M injection more than 9 months ago, and the next scheduled maintenance dose of the PP3M should be administered to said patient, comprising:
 (1) administering intramuscularly in the deltoid muscle of said patient a first reinitiation loading dose of 150 mg eq. of monthly injectable paliperidone palmitate depot (PP1M);
 (2) administering intramuscularly in the deltoid muscle of said patient a second reinitiation loading dose of 100 mg eq. of PP1M on about the 4th day to about the 12th day after administering said first reinitiation loading dose;
 (3) administering intramuscularly in the deltoid or gluteal muscle of said patient a first reinitiation maintenance dose of 50 mg eq. to about 150 mg eq. of PP1M on about the 23th day to about the 37th day after administering said second reinitiation loading dose;
 (4) administering intramuscularly in the deltoid or gluteal muscle of said patient a second reinitiation maintenance dose of from about 50 mg eq. to about 150 mg eq. of PP1M on about the 23rd day to about the 37th day after administering of the first reinitiation maintenance dose;
 (5) administering intramuscularly in the deltoid or gluteal muscle of said patient a third reinitiation maintenance dose of from about 50 mg eq. to about 150 mg eq. of PP1M on about the 23rd day to about the 37th day after administering of the second reinitiation maintenance dose; and
 (6) administering intramuscularly in the deltoid or gluteal muscle of said patient from about 175 mg eq. to about 525 mg eq. of PP3M on about the 23rd day to about the 37th day after administering of the last reinitiation maintenance dose of monthly injectable paliperidone palmitate.

2. The method of claim 1, wherein said patient is in need of treatment for psychosis.

3. The method of claim 1, wherein said patient is in need of treatment for schizophrenia.

4. The method of claim 1, wherein said patient is in need of treatment for bipolar disorder.

5. A dosing regimen for administering an injectable paliperidone palmitate depot to a patient in need of treatment for psychosis, schizophrenia or bipolar disorder that has been treated with PP3M, wherein said patient had been last administered a PP3M injection 4 to 9 months ago and the next scheduled maintenance dose of PP3M should be administered to said patient, comprising:

(1) administering intramuscularly in the deltoid muscle of said patient a first reinitiation loading dose of PP1M;

(2) administering intramuscularly in the deltoid muscle of said patient a second reinitiation loading dose of PP1M on about the 4th day to about the 12th day after administering of said first reinitiation loading dose; and (3) administering intramuscularly in the deltoid or gluteal muscle of said patient a reinitiation dose of PP3M on about the 23rd day to about the 37th day after administering the second reinitiation loading dose of PP1M wherein said first and second reinitiation loading doses and the reinitiation PP3M dose are selected from the table below based on the amount of the missed dose

| Missed Dose of PP3M | Reinitiation Doses of PP1M | Reinitiation Doses of PP3M |
| --- | --- | --- |
| 175 mg eq. | 50 mg eq. | 175 mg eq. |
| 263 mg eq. | 75 mg eq. | 263 mg eq. |
| 350 mg eq. | 100 mg eq. | 350 mg eq. |
| 525 mg eq. | 100 mg eq. | 525 mg eq. |

6. The method of claim 5, wherein said patient is in need of treatment for psychosis.

7. The method of claim 5, wherein said patient is in need of treatment for schizophrenia.

8. The method of claim 5, wherein said patient is in need of treatment for bipolar disorder.

9. The method of claim 5 wherein the second reinitiation dose of PP1M is administered about 7 days after administering said first reinitiation loading dose of PP1M.

10. The method of claim 9 wherein the second reinitiation dose of PP1M is administered 7 days after administering said first reinitiation loading dose of PP1M.

11. The method of claim 5 wherein the reinitiation dose of PP3M is administered about 30 days after administering said second reinitiation loading dose of PP1M.

12. The method of claim 11 wherein the reinitiation dose of PP3M is administered 30 days after administering said second reinitiation loading dose of PP1M.

13. The method of claim 5 wherein the reinitiation dose of PP3M is administered about a month after administering said second reinitiation loading dose of PP1M.

14. The method of claim 11 wherein the reinitiation dose of PP3M is administered a month after administering said second reinitiation loading dose of PP1M.

15. The method of claim 1 wherein the second reinitiation loading dose of PP1M is administered about 7 days after administering said first reinitiation loading dose of PP1M.

16. The method of claim 15 wherein the second reinitiation loading dose of PP1M is administered 7 days after administering said first reinitiation loading dose of PP1M.

17. The method of claim 1 wherein the first reinitiation maintenance dose of PP1M is administered about 30 days after administering said second reinitiation loading dose of PP1M.

18. The method of claim 1 wherein the first reinitiation maintenance dose of PP1M is administered 30 days after administering said second reinitiation loading dose of PP1M.

19. The method of claim 1 wherein the second reinitiation maintenance of PP1M is administered about 30 days after administering said first reinitiation maintenance dose of PP1M.

20. The method of claim 1 wherein the second reinitiation maintenance of PP1M is administered 30 days after administering said first reinitiation maintenance dose of PP1M.

21. The method of claim 1 wherein the third reinitiation maintenance of PP1M is administered about 30 days after administering said second reinitiation maintenance dose of PP1M.

22. The method of claim 1 wherein the third reinitiation maintenance of PP1M is administered 30 days after administering said second reinitiation maintenance dose of PP1M.

23. The method of claim 1 wherein PP3M is administered about 30 days after administering said last reinitiation maintenance of PP1M.

24. The method of claim 1 wherein PP3M is administered 30 days after administering said last reinitiation maintenance of PP1M.

25. The method of claim 1 wherein PP3M is administered about a month after administering said last reinitiation maintenance of PP1M.

26. The method of claim 1 wherein PP3M is administered a month after administering said last reinitiation maintenance of PP1M.

27. The method of claim 1 further comprising administering intramuscularly in the deltoid or gluteal muscle of said patient a fourth reinitiation maintenance dose of from about 50 mg eq. to about 150 mg eq. of PP1M on about the 23rd day to about the 37th day after administering the third reinitiation maintenance dose.

28. The method of claim 27 wherein said fourth reinitiation maintenance of PP1M is administered about 30 days after administering said third reinitiation maintenance dose of PP1M.

29. The method of claim 28 wherein said fourth reinitiation maintenance of PP1M is administered 30 days after administering said third reinitiation maintenance dose of PP1M.

* * * * *